(12) United States Patent
Vitali et al.

(10) Patent No.: US 6,587,722 B2
(45) Date of Patent: Jul. 1, 2003

(54) DEVICE FOR DETERMINING THE EFFECTIVENESS OF STIMULATION IN AN ELECTRICAL HEART STIMULATOR

(75) Inventors: Luca Vitali, Turin (IT); Luigi Silvestri, Turin (IT)

(73) Assignee: Sorin Biomedica Cardio S.p.A., Saluggia (IT)

( * ) Notice: Subject to any disclaimer, the term of this patent is extended or adjusted under 35 U.S.C. 154(b) by 213 days.

(21) Appl. No.: 09/836,841

(22) Filed: Apr. 17, 2001

(65) Prior Publication Data

US 2002/0013611 A1 Jan. 31, 2002

(30) Foreign Application Priority Data

Apr. 18, 2000 (EP) ............................. 00830297

(51) Int. Cl.[7] ............................................. A61N 1/362
(52) U.S. Cl. ....................................................... 607/27
(58) Field of Search ............................... 607/27, 28, 9, 607/11, 13; 600/510

(56) References Cited

U.S. PATENT DOCUMENTS

| | | |
|---|---|---|
| 3,949,758 A | 4/1976 | Jirak |
| 4,373,531 A | 2/1983 | Wittkampf et al. |
| 4,399,818 A | 8/1983 | Money |
| 4,674,508 A | 6/1987 | DeCote, Jr. |
| 4,686,988 A | 8/1987 | Sholder |
| 4,729,376 A | 3/1988 | DeCote, Jr. |
| 4,817,605 A | 4/1989 | Sholder |
| 4,821,724 A | 4/1989 | Whigham et al. |
| 4,878,497 A | 11/1989 | Callaghan et al. |
| 5,172,690 A | 12/1992 | Nappholz et al. |
| 5,265,603 A | 11/1993 | Hudrlik |
| 5,324,310 A | 6/1994 | Greeninger et al. |
| 5,330,512 A * | 7/1994 | Hauck et al. ............. 607/28 |
| 5,350,410 A | 9/1994 | Kleks et al. |
| 5,411,533 A | 5/1995 | Dubreuil et al. |
| 5,417,718 A | 5/1995 | Kleks et al. |
| 5,443,485 A * | 8/1995 | Housworth et al. ........... 607/28 |
| 5,476,487 A | 12/1995 | Sholder |
| 5,561,529 A | 10/1996 | Tanaka et al. |

(List continued on next page.)

FOREIGN PATENT DOCUMENTS

| | | |
|---|---|---|
| EP | 0 561 781 B1 | 9/1993 |
| EP | 0 717 646 B1 | 6/1996 |
| EP | 0 765 177 B1 | 4/1997 |
| EP | 0 850 662 A3 | 7/1998 |
| EP | 0 850 662 A2 | 7/1998 |
| EP | 0 941 744 A1 | 9/1999 |

OTHER PUBLICATIONS

Search Report for Counterpart EP Application No. 00830297.8 (2 pages).

Primary Examiner—Jeffrey R. Jastrzab
(74) Attorney, Agent, or Firm—Popovich & Wiles, P.A.

(57) ABSTRACT

A device for determining the effectiveness of the electrical stimulation of heart muscle from a signal having a post-potential component and, with effective stimulation, a superimposed evoked response component. The device includes a differential stage with a first input for application of the signal and a second input for application of a feedback signal. The differential stage generates a corresponding output signal whose level is determined by the levels of the signals present at the first and said second inputs. A comparator stage has feedback units able to act on the second input in a follower relationship with respect to the signal present at the first input avoiding saturation of the differential stage. The feedback units generate at least one compensation signal indicating the variation in the signal present at the first input over time. The compensation signal is indicative of the evoked response superimposed on the post-potential component.

22 Claims, 4 Drawing Sheets

U.S. PATENT DOCUMENTS

| | | | |
|---|---|---|---|
| 5,697,957 A | * 12/1997 | Noren et al. | 607/28 |
| 5,718,720 A | 2/1998 | Prutchi et al. | |
| 5,741,312 A | 4/1998 | Vonk et al. | |
| 5,843,136 A | 12/1998 | Zhu et al. | |
| 5,861,012 A | 1/1999 | Stroebel | |
| 5,873,898 A | 2/1999 | Hemming et al. | |
| 5,954,756 A | 9/1999 | Hemming et al. | |
| 6,052,622 A | * 4/2000 | Holmstrom | 607/28 |
| 6,427,085 B1 | * 7/2002 | Boon et al. | 607/28 |
| 6,501,989 B1 | * 12/2002 | Uhrenius et al. | 607/28 |

* cited by examiner

DEVICE FOR DETERMINING THE EFFECTIVENESS OF STIMULATION IN AN ELECTRICAL HEART STIMULATOR

FIELD OF THE INVENTION

This invention relates to a device for determining the effectiveness of stimulation in an electrical heart stimulator.

BACKGROUND OF THE INVENTION

In the practice of heart stimulation, one of the characteristic features of a stimulator is the length of its service life, that is the service life of the power source (typically a battery) which powers it. This length of time is directly linked to the power consumption of the stimulating system, a significant component of which is the energy released in the form of electrical stimulation applied to the heart muscle.

The significance of this aspect is particularly obvious in systems which are designed to be implanted in a patient's body. A stimulus is effective (and in this case it is said that it has "captured" the heart) if its energy exceeds a minimum value, the so-called "stimulation threshold" or "capture threshold". This threshold value depends on the stimulating system and the characteristics of the heart muscle involved.

In particular, it cannot be assumed that the value of the stimulation threshold remains constant over time. Because in current practice the energy of the stimulus is decided upon and set by the cardiologist when the unit is checked, and cannot be altered until a subsequent check, the solution currently adopted is to set the energy of the stimulus at a value substantially higher than the stimulation threshold. This is in order to guarantee effective stimulation for different stimulation threshold conditions. A consequence of this is the fact that the energy delivered by the heart stimulator with every stimulus can be very much greater (even four times or more greater) than the minimum which is necessary and sufficient.

There is therefore in general a need to have systems such that energy can be saved when providing the stimulating action, while at the same time ensuring that the effectiveness of the stimulation is constant. This is in order to provide a significant advantage in the design of a heart stimulator, among other things providing a longer service life for the device.

As a rule, satisfaction of the requirement stated above requires that the stimulator be capable of establishing whether it has successfully induced contraction of the heart muscle when delivering a stimulus. With this information the system can establish the value of the stimulation threshold sufficiently frequently (and even for each individual stimulus) and adjust the energy of the stimulus to minimize the proportion of energy which is actually wasted.

In general terms, the stimulus delivery system can be regarded as an electrical circuit comprising the stimulator itself, the electrode which delivers the stimulus to the heart and the complex of physiological tissues which returns the stimulus current to the stimulator: the area of heart muscle in contact with the terminal of the stimulation electrode constitutes the "active" part of the electric circuit.

The behavior of this circuit has special features which are generally known and do not therefore need to be referred to in detail here. This is apart from one aspect, which is linked to the fact that once the stimulus—comprising a short electrical pulse of the magnitude of the order of a few volts and lasting of the order of a millisecond—has come to an end, part of its energy remains trapped in the circuit, giving rise to an appreciable potential difference which decreases over time as this energy is dissipated until the entire system returns to its initial conditions over a period of a few hundred milliseconds.

This tail electrical potential, usually known as the post-potential or stimulation artifact, or again the electrode polarization potential, may have a magnitude—measured immediately after stimulation—which is still of the order of a hundred millivolts. A typical profile for a post-potential signal of the type described is illustrated in profile a) of FIG. 1.

On the other hand, in addition to mechanical contraction of the muscle, the heart's response to an effective stimulus is also manifested by an electrical response, known as the evoked potential, which is linked to the electrical activity of the cells during the contraction stage. This electrical potential (having the characteristics of a pulse of varying shape, lasting a few tens of milliseconds and of a magnitude of a few millivolts, which typically arises 10 to 50 milliseconds after the stimulus) can also be observed in the stimulator circuit, but superimposed on the stimulation post-potential. The magnitude of the latter may however be such as to render identification of the evoked response in the heart difficult.

A typical profile of an evoked response signal is shown in the bottom diagram, indicated by b) in FIG. 1. It will be appreciated that the two diagrams a) and b) in FIG. 1 are not to scale and that typically the peak for the post-potential signal may correspond to a value 10 to 100 times greater than the peak value for the evoked response signal. The waveform which can be observed after each effective stimulus is the result of the overlap (algebraic sum) of the two waveforms illustrated. If the stimulus is not effective, the component due to the evoked response (diagram b) will obviously be absent.

The complexity of problems described above has already been considered by the art through the adoption of a variety of solutions. There are systems in which detection of the evoked response is based on an analog filtering process with amplification of the potential measured on the stimulating electrode in comparison with a reference potential. Solutions of this type are described in for example documents EP-A-0 717 646, U.S. Pat. No. 5,561,529, U.S. Pat. No. 5,443,485, U.S. Pat. No. 5,718,720 and U.S. Pat. No. 5,873,898.

In substance these solutions provide for the greatest possible amplification of the evoked response and attempt to suppress the undesired part due to the stimulus post-potential as much as possible (typically through filtering).

This process has however proved difficult because, in the first place, as has been seen, the signal corresponding to the stimulus post-potential usually has a magnitude which is very much greater than the signal corresponding to the heart's evoked response, and the frequency spectra of the two signals in question largely overlap and therefore cannot be separated by filtering in the frequency field.

In particular an amplification and linear filtering system can easily be saturated by the post-potential signal, thus making it impossible to detect any evoked response by the heart.

The functioning of other systems is based on the presence or absence of events which are indirectly linked with capture, such as e.g., the occurrence of spontaneous heart contractions before and after the stimulus which are detected by methods which are well-known in the art of heart stimulation (see for example documents EP-A-0 850 662 and U.S. Pat. No. 5,861,012).

Of the methods based on knowledge of past events, some operate by comparing the profile of the potential after the stimulus with a sample signal in which only the post-potential is present without the evoked response. In order to establish that the heart muscle has been captured in a generic stimulus, the corresponding signal is compared with the sample signal, and capture is therefore stated to have occurred when the differences with respect to the sample are sufficiently large.

Solutions of this type are described in documents U.S. Pat. No. 4,674,508, , U.S. Pat. No. 4,686,988, U.S. Pat. No. 4,729,376, U.S. Pat. No. 4,817,605, U.S. Pat. No. 5,350,410, and U.S. Pat. No. 5,417,718.

These systems have two main disadvantages. First, in order to obtain a sample signal, it is necessary to perform a specific operation comprising the release of a stimulus which is reliably ineffective (there are various techniques for achieving this result) followed by recording of the response generated. Second, the form and amplitude of the stimulation artifact can change, and in fact change in relation to the energy of the stimulus. Thus, the operation described in the preceding paragraph must theoretically be performed whenever the characteristics of the stimulus are changed. These disadvantages make the above-mentioned systems more complex to construct, for equal effectiveness.

Yet other systems attempt to improve the discernibility of the heart response by reducing the magnitude of the post-potential or stimulation artifact as much as possible. These systems nevertheless require the use of special electrodes in which the phenomenon of the post-stimulation potential is minimized. These systems attempt to compensate for the stimulation post-potential by injecting into the circuit an amount of electrical energy identical and contrary to that which is expected as a residue. Examples of solutions of this type are found in documents U.S. Pat. No. 4,373,531, , U.S. Pat. No. 4,399,818, U.S. Pat. No. 4,821,724, U.S. Pat. No. 5,172,690, U.S. Pat. No. 5,741,312 and U.S. Pat. No. 5,843,136.

In particular, systems based on post-stimulus compensation have proved to be subject to appreciable criticality. Even a small error in estimation of the energy required is in fact sufficient to make it difficult to distinguish the evoked response. Furthermore, the use of special stimulating electrodes (typically of the type known as "steroid eluting") constitutes a constraint which is not always accepted in the practice of heart-stimulating implants.

Of the systems described above, some function intrinsically through observing a series of successive stimuli, which makes it impossible to detect capture stimulus by stimulus. In this respect reference may be made, for example, to documents EP-A-0 765 177, U.S. Pat. No. 4,674,508, U.S. Pat. No. 4,729,376, U.S. Pat. No. 4,817,605, U.S. Pat. No. 5,741,312, U.S. Pat. No. 5,476,487 and U.S. Pat. No. 5,411,533. Yet other systems depend on the use of bipolar electrodes, which imposes a constraint upon their use. Examples of this type are documented in EP-A-0 561 781, U.S. Pat. No. 3,949,758, U.S. Pat. No. 4,817,605, U.S. Pat. No. 4,878,497, U.S. Pat. No. 5,265,603 and U.S. Pat. No. 5,324,310.

It will be appreciated that some of the documents provided as examples of various categories of solutions considered above have been cited more than once. This is due to the fact that in various cases a document constitutes an example of more than one of the solutions considered from time to time.

SUMMARY OF THE INVENTION

This invention therefore has the purpose of providing a heart stimulating system capable of simultaneously satisfying one or more of the following requirements:

1) the possibility of using it regardless of the type of electrode available, whether of the single pole or bipolar type, avoiding the need to use electrodes having special characteristics and/or of a special type,
2) the possibility of doing away with the acquisition of a reference sample,
3) limiting observation to the events which occur immediately after stimulation, without the need to observe other indirect events (e.g., spontaneous sensing etc.),
4) the possibility of avoiding methods of processing the stimulus post-potential (either by filtering means or using electrical compensation methods) in order to eliminate it or reduce its magnitude, and
5) the possibility of deciding on the relative effectiveness, stimulus by stimulus, without the need to perform a statistical observation of a number of consecutive stimuli.

The solution according to the invention is based on a circuit capable of tracking the artifact of stimulation while avoiding saturation of the amplification stage, so as to be able to convert the signal detected at the electrode into a series of electrical pulses whose sequence in time reproduces the profile of the potential (post-potential plus any evoked response). Processing of the above-mentioned pulses, based on an algorithm used by a processing unit located on board the stimulator, and therefore capable of being implanted, makes it possible to establish whether the heart has been captured by the stimulus, reliably and with certainty.

This invention is a device for determining the effectiveness of electrical stimulation of heart muscle from a signal comprising a post-potential component having, in the event of effective stimulation, a superimposed evoked response component. The device comprises a differential stage with a first input for application of the signal and a second input for application of a feedback signal, the differential stage generating a corresponding output signal whose level is determined by the levels of the signals present at the first and said second inputs; and a comparator stage including a feedback unit configured to act on the second input in a follower relationship to the signal present at the first input avoiding saturation of the differential stage; the feedback unit being configured to generate at least one compensating signal indicative of the variation of the signal present at the first input over time, the at least one compensating signal being indicative of the presence of the evoked response. The comparator stage may comprise at least two threshold levels which, when reached by the output signal from the differential stage, are indicative of possible saturation of the differential stage relative to its linear functioning dynamics. The comparator stage also may comprise at least one further threshold defining a field of values for the output signal from the differential stage in which the feedback unit is substantially inactive. The feedback unit may be configured to generate first and second compensation signals which are indicative, respectively, of the divergence between the output signal from the differential stage in a first and a second direction, respectively, with respect to a selected reference level. The feedback unit also may be configured to apply a signal obtained from the sum of the first and the second compensation signals to the second input of the differential stage. The sum may have different signs. The feedback unit may have an integrator stage configured to generate a signal applied to the second input by integration.

The compensating signal may be a pulsed signal in which the frequency of the pulses is indicative of the difference between the output signal from the differential stage and a selected reference level. The comparator stage may be configured to generate first and second compensation signals of the pulsed type, in which the pulse frequency is indicative of the derivative of the signal present at the first input with respect to time, the first and second compensation signals being generated alternately between them according to the sign of the derivative.

The device may also include a counter, wherein the first and second compensation signals are input respectively as increasing and decreasing signals to the counter, the progression of the count in the counter over a selected period of time comprising a sequence of count signal values indicative of the effectiveness of the stimulation pulse. The counter may be configured so as to be zeroed corresponding to the action of electrically stimulating the heart muscle and may be enabled after a predetermined time interval following stimulation of the heart muscle. The counter may be enabled for the purposes of performing the corresponding count during a time window of a size determined from the stimulating effect. The time window may range from 50 to 60 milliseconds.

The device may further comprise a processing logic module which is capable of applying to the count signal values from the counter during the selected period of time at least one criteria for identifying the effectiveness of stimulation selected from the group of:

1) whether the sum of all the negative values which are greater in absolute value than a selected threshold value exceeds a predetermined limit,
2) whether the maximum value of the count signal values, in modulus and sign, is greater than the first value of the count signal values incremented by a specified amount, and
3) whether reduction of the sequence of the count signal values by interpolation into a series of segments of a straight line identified by their corresponding angular coefficients, with subsequent comparison of the angular coefficients with corresponding pairs of selected limit values results in at least one of the angular coefficients exceeding the corresponding pair of limit values.

The processing logic module may be configured to generate an output signal indicative of effective stimulation when an affirmative result is obtained from one of the criteria, to apply the criteria in sequence, passing on to the next criterion if a negative result is obtained from one of the criteria, or to generate an output signal indicative of ineffective stimulation when all three of the criteria yield a negative outcome. The device may further include means for detecting excursion of the count signal values during the selective period of time between a selected maximum and a selected minimum value and for declaring that the stimulating action is ineffective if the detected excursion is less than a predetermined limit. The processing logic module then may be configured to detect a difference between a maximum value and a minimum value of the sequence of count signal values subjected to the third criterion and to apply the third criterion only if the difference between the maximum value and the minimum value is greater than a predetermined limit. The processing logic module may be configured to avoid application of the third criterion when the difference between the maximum value and the minimum value is less than the predetermined limit.

The processing logic module may be selected from:
a filtering module to reduce the spectral content of the signal transferred to the logic module at higher frequencies,
a module to differentiate the sequence of values subjected to the filtering, and
a module to translate the values obtained from this differentiation in such a way that the last of them is always zero.

BRIEF DESCRIPTION OF THE PREFERRED EMBODIMENTS

Figure 2:
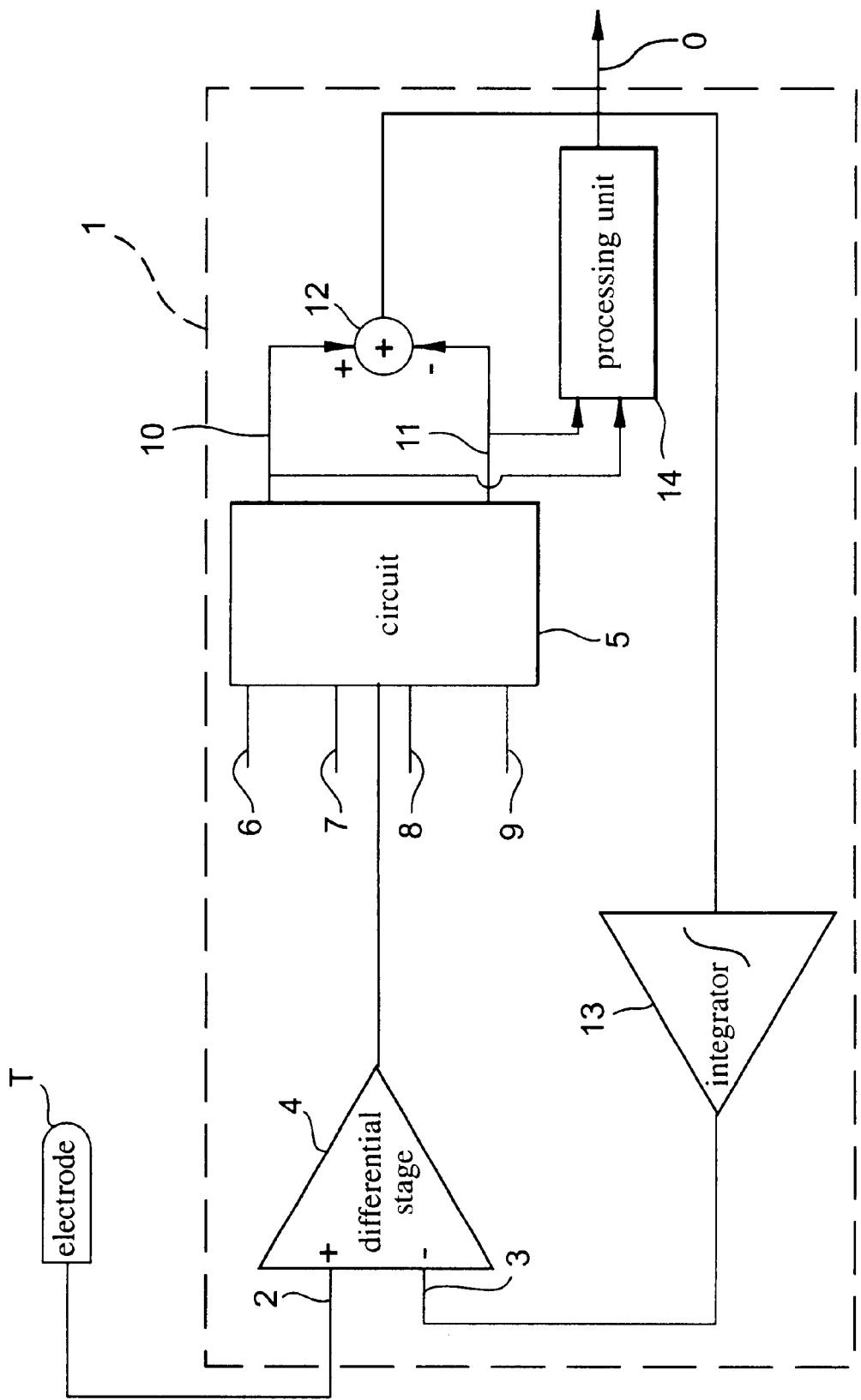
FIG. 2 shows the circuit structure of a device according to the invention in the form of a block diagram.

Turning now to the drawings, FIG. 2 illustrates a device, indicated generically by 1, which is designed to be associated with a heart stimulator device, which is not illustrated but is of a known type. In particular, device 1 is designed to be constructed as an integral part of the heart stimulator circuit and as such is capable of being implanted into a patient's body.

Figure 1:
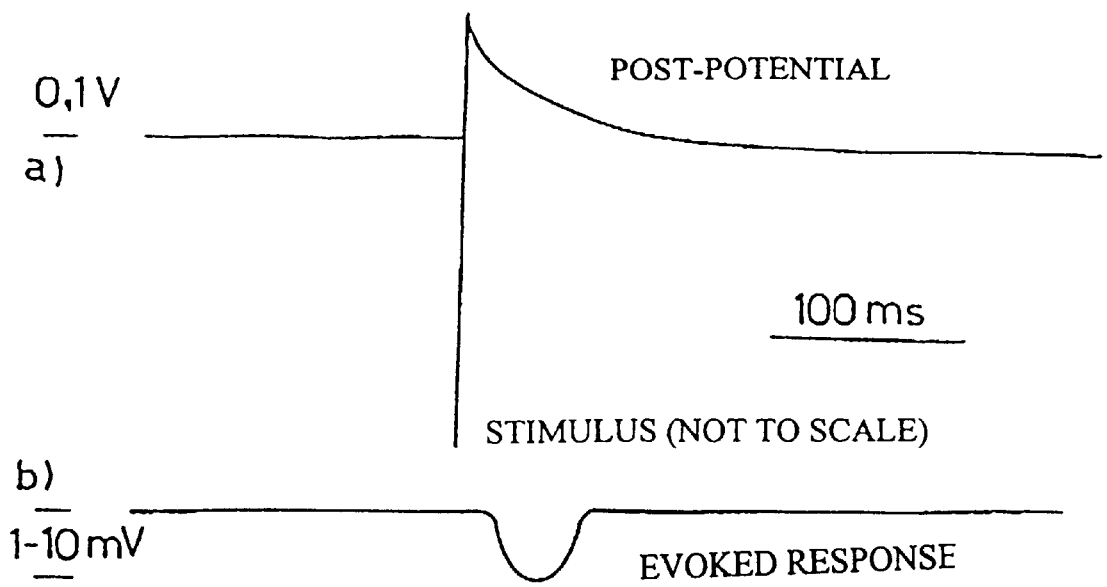
FIG. 1 illustrates typical voltage vs. time profiles of the post-potential (profile a) and evoked response (profile b) signals that can be detected following the application of a stimulating electrical pulse generated by an electrical stimulator to the heart muscle.

Device 1 is designed to be connected to a stimulation electrode T so that it can detect a signal corresponding to the signals illustrated in FIG. 1. This is with the object of being capable of transmitting, on an output line indicated generically by O, a signal which is indicative of the fact that a stimulus applied to the heart muscle through electrode T has effectively achieved "capture" of the heart muscle. The signal present on line O typically comprises a logic signal which has two different levels (a "high" or "low" respectively or vice versa, depending upon the fact whether capture has occurred or not).

The signal present on line O can therefore be processed within the logic circuitry of the stimulator in order to perform the modification, adjustment, reprogramming, etc., of a stimulation strategy provided through the device itself, or to record any changes in the stimulation threshold, or abnormalities in the effectiveness of stimulation, for statistical and diagnostic use by the doctor monitoring the stimulator implant. All this takes place in accordance with criteria which are in themselves known and which, as such, are not in themselves significant for the purpose of understanding or implementing this invention. The criteria used to obtain the signal (post-potential plus evoked response—if present) are described above. These criteria and the signal to be fed to the circuitry of device 1 are known to those of skill in the art.

All of this can take place on the basis of various criteria that are known in the art. This applies in particular as regards the possibility of obtaining the aforesaid signal, for example, from an electrode T which is different from the electrode which performs the action of stimulating the heart muscle. Here again the corresponding criteria for obtaining the aforesaid signal must be regarded as being in themselves known, and therefore do not require detailed description here, and also because these are in themselves not significant for the purpose of understanding and implementing this invention.

Within the scope of the circuit diagram for device 1 illustrated in FIG. 2, references 2 and 3 represent the two input lines to differential stage 4 which has a high gain. Typically this may be an operational amplifier with a gain value G equal to, for example, one thousand.

As is well known, if inputs 2 and 3 to amplifier 4 were at the same level of potential, amplifier 4 would have a fixed value (e.g., but not necessarily equal to 0 volt) at its output. This fixed potential value can be regarded as a reference potential (see level VR in diagram a) in FIG. 3). One of the inputs to amplifier 4 (in the embodiment illustrated here this is the non-inverting input, but it may also be inverting input 3) is designed to receive (e.g., from stimulating electrode T) the signal corresponding to profiles a) and b) in FIG. 1, that is a signal corresponding to the post-potential signal with a possibly superimposed evoked response signal (when present; the detection of which is the basis of the operation of the device in FIG. 2).

If the other input (in the case illustrated inverting input 3) to stage 4 were set at a fixed potential, the output from amplifier 4 would always be in a saturated condition at one or other extreme of the amplifier's output dynamic. This would be because, in addition to the non-ideality of the behavior of the circuit, a minimum differential signal at the input is likely to give rise to very great changes in the voltage of the output signal from amplifier 4. All this corresponds to criteria well known in the art, in particular in relation to operational amplifiers comprising a typical example of the construction/use of differential stages with a very high gain.

The operation of the circuitry of device 1 is based on keeping amplifier 4 always in a condition of linear operation by using a feedback system involving circuit 5. Circuit 5 essentially comprises a complex of threshold comparators having a certain number of threshold levels such as, e.g., four levels indicated by 6, 7, 8 and 9 respectively. The diagrammatical representation of the threshold levels as possible contact pins for circuit 5 is to indicate that these levels can be selectively adjustable. In substance, whatever the number of levels and the manner in which these are constructed or connected, circuit 5 is constructed so that when the output voltage from amplifier 4 reaches a predetermined value, by differing from the reference potential in one direction or the other, which is still within the limits or the possibility of linear functioning for amplifier 4, circuit 5 generates current (or voltage) pulses at its corresponding outputs 10, 11. Outputs 10 and 11, when summed, with their signs, at node 12, are applied to integrator 13, which is designed to close the feedback loop to input 3 of amplifier 4.

In particular, all the parts included in the feedback loop are configured in such a way that the feedback signal is capable of causing a change in the level of the signal at input 3 capable of bringing the output from amplifier 4 back toward the reference potential. When the output from amplifier 4 returns within predetermined limits the current or voltage pulses applied to integrator 13 die away and the voltage at input 3 thereafter remains constant.

In the embodiment illustrated, there are four thresholds for circuit 5. Two of these, thresholds 6 and 9, identify the levels of potential outside which activation of the compensating pulses generated on output lines 10 and 11 is to begin. The other two thresholds, indicated by references 7 and 8, which are closer to the reference potential, establish the re-entry levels, that is the potential level at which activation of the compensating pulses present on outputs 10 and 11 is caused to cease.

By way of example, it can be imagined that thresholds 6 and 9 are one volt above and below the reference potential respectively, with thresholds 7 and 8 set at 0.5 volts above and below the reference potential respectively. The corresponding signal levels are therefore shown by V6 and V9, on the one hand, and by V7 and V8, on the other hand, in profile a) in FIG. 3.

Circuit 5 can be constructed in various ways following criteria which are in themselves known on the basis of the functional requirements specified here. In practice, when the output signal from amplifier 4 exceeds level V6 (corresponding to threshold 6) a succession of pulses V10, each of a predetermined length (which can be freely set, fixed or variable with time) is generated at output 10 which, when applied to summing node 12 (e.g., with a positive sign) act on amplifier 4 through integrator 13 in such a way as to cause the output signal from amplifier 4 to decrease gradually towards reference level VR.

When, on the other hand, the output signal from amplifier 4 descends below threshold level V9 (corresponding to threshold 9) a succession of pulses V11, each of a predetermined length (which can be freely set, fixed or variable with time) is generated at output 11. When V11 is applied to summing node 12 (e.g., with a negative sign), feed back to input 3 of amplifier 4 through an integrator 13 causes the output signal from amplifier 4 to rise again towards reference voltage VR.

Figure 3:
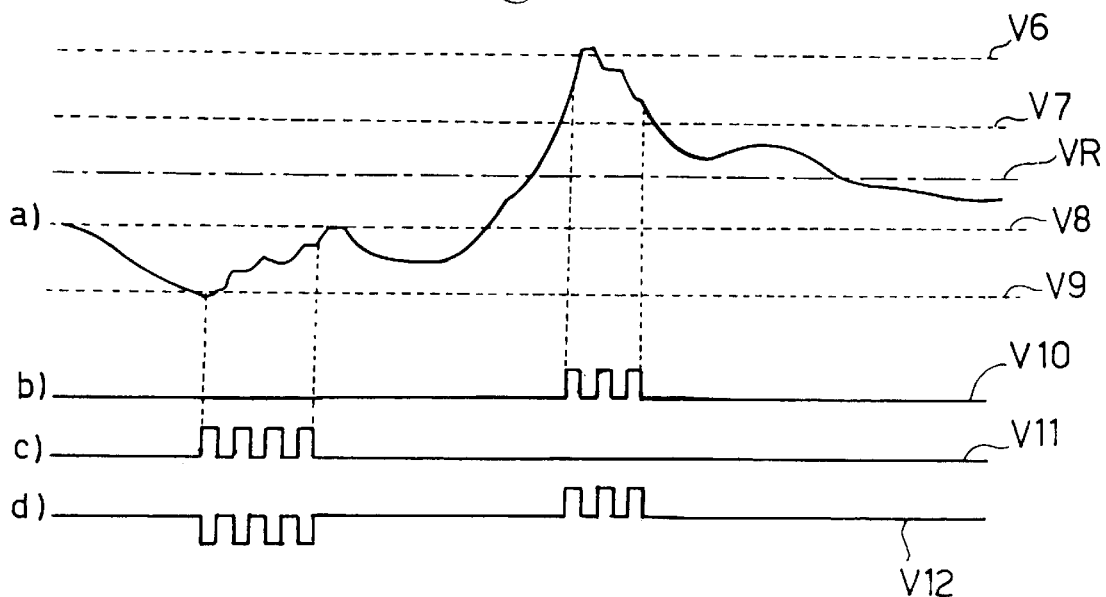
FIGS. 3 and 4 show four superimposed diagrams indicated, respectively, by reference lines a), b), c) and d), illustrating the typical voltage vs. time profiles of some signals which can be detected by the device according to the invention.

Possible profiles for signals V10 and V11 are shown in diagram b) and c) in FIG. 3, which is to be regarded as being synchronously coordinated with diagram a) in the same FIG. Diagram d) merely shows signal V12 which can be detected at the output from summing node 12 which corresponds in practice to the sum of signals V10 and V11 (which for obvious reasons are never present simultaneously).

A person of skill in the art will readily appreciate that the solution described lends itself to numerous construction variants having identical functional results. For example, the thresholds in circuit 5 could be less than four. Thresholds 7 and 8 could both coincide with the reference potential VR or could be entirely eliminated, establishing a fixed time for the compensation period from the outset. Furthermore, the magnitude of the compensation current or voltage corresponding to signal V12 could be made variable with time, e.g., so as to cause it to increase in absolute value with respect to a minimum value so as to ensure faster following where very rapid changes occur in the output signal from amplifier 4, thus achieving compression of the signal dynamics.

When the output voltage from differential amplifier 4 remains within the safeguarding limits (represented by thresholds 7 and 8 in the embodiment illustrated), the current or voltage present at the output from node 12 is zero, the voltage at point 3 does not change and amplifier 4 is free to amplify the difference between the potentials at inputs 2 and 3.

The feedback loop described thus acts in such a way that input 3 of differential amplifier 4 follows the changes in potential at input 2 in such a way as to keep amplifier 4 away from saturation conditions at all times. It will therefore be appreciated in more general terms that the feedback system illustrated here, although corresponding to a preferred embodiment of the invention, is suitable for an almost infinite number of functionally equivalent variants.

As a by-product of the following process described, two signals of the digital type (that is signals which have only two potential values indicated conventionally as "0" or "signal not active" and "1" or "signal active") corresponding to signals V10 and V11 respectively are generated within block 5. In particular, signal V10 is associated with the condition given by the fact that the output signal from amplifier 4 exceeds the upper safeguarding limit identified by threshold 6, while signal V11 corresponds to the condition in which the output signal from amplifier 4 descends below the lower safeguarding limit identified by threshold 9.

The above-mentioned pulse signals are activated when the comparator system in circuit 5 shows the need to compensate for a change in potential at input 2 in order to adjust the input potential towards that level. It is therefore possible to regard signals 10 and 11 (which can be generated within block 5 in accordance with known criteria, and which therefore do not require a detailed description here) as compensating pulse signals.

In the embodiment illustrated, a train of pulses (of a duration which is predetermined, constant or variable in accordance with a predetermined relationship) is generated at outputs 10 or 11 of circuit 5 as long as the voltage of the signal at the output from amplifier 4 does not return within the reference potential specified by thresholds 7 and 8 after having exceeded thresholds 6 and 9. In another possible implementation, pulses 10 and 11 may be activated when corresponding threshold levels 6 or 9 respectively are exceeded by the output from amplifier 4 and remain active continuously until the voltage of the signal at the output from amplifier 4 returns within the reference potential established by thresholds 7 and 8.

If it is imagined that a constant signal is applied to input 2 of amplifier 4 it is obvious that, with the exception of an initial transient, neither signal V10 nor signal V11 will ever adopt an active value (logic value "1"). If it is imagined that a potential which increases linearly over time is applied to input 2 it is obvious that in the system described there will be periodical activation of signal V10 by trains of pulses or by individual pulses, at intervals which become closer in time the faster the change in the potential at point 2 with time. In other words, the average number of pulses generated per unit time within the scope of signal 10 is proportional to the derivative of input signal 2 with respect to time.

If the sign of the change in potential at input signal 2 is reversed, the pulses will be generated in the form of signal V11, in the same way as in the situation above. In general, whatever the form of the signal applied to input 2, there will be a series of pulses on line 10 whenever the input signal increases, in faster succession the faster the rate of growth of the input signal, while on line 11 there will be pulses when the potential at the input decreases over time, in faster succession the faster the rate of change in the signal.

The average frequency of the compensating pulses generated will therefore be proportional to the derivative (and, more generally, the variation) in the signal applied at input 2 with respect to time, while the sign of the variation or derivative will be indicated by which of the compensating signals (V10 or V11) is periodically activated. This process will take place independently of the absolute value of the input potential, that is, independently of the initial magnitude of the stimulus post-potential.

Figure 4:
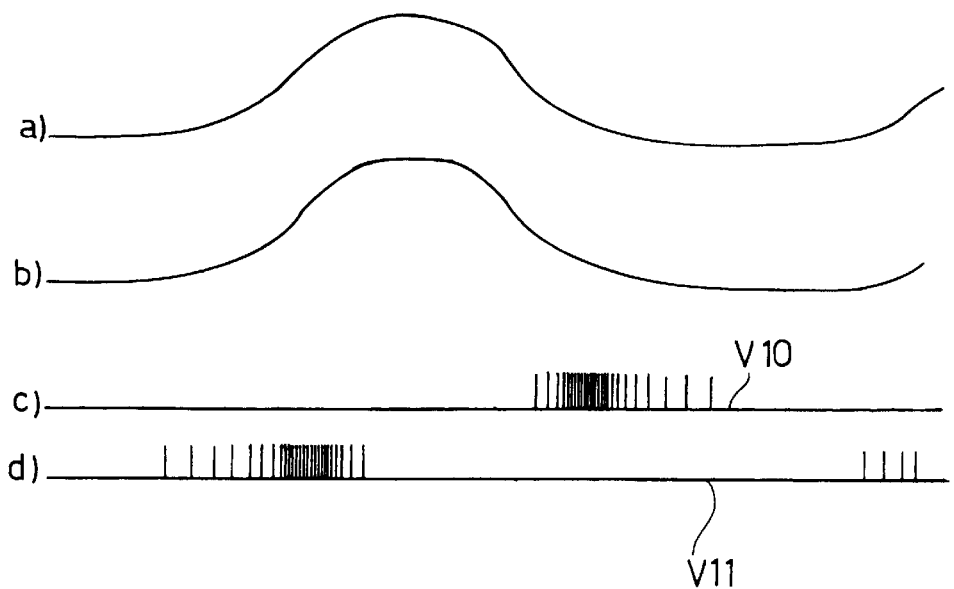

Observation of the sequence of pulses generated by the system in a suitable time interval after application of the stimulation to the heart muscle can therefore be used to deduce the presence of any evoked response (profile b) in FIG. 1). In FIG. 4, diagram a) represents a possible profile of the voltage applied to input 2 of the circuit, while diagram b) indicates the profile of the voltage present at input 3 within the scope of the circuit in FIG. 1. Diagrams c) and d) on the other hand indicate a possible profile of signals V10 and V11 corresponding to the profiles found for the signals represented by diagrams a) and b).

Thanks to the compensating action the voltage at input 3 periodically follows that applied to input 2 in such a way that under the operating conditions assumed differential amplifier 4 is never in a saturated condition. Signals V10 and V11 constitute a final product of the operation of the circuit and contain information that must be processed subsequently, that is information relating to the effectiveness of the stimulus. The two signals on lines 10 and 11 are therefore sent to processing unit 14 which generates the output signal O from the above-mentioned signal.

Figure 5:
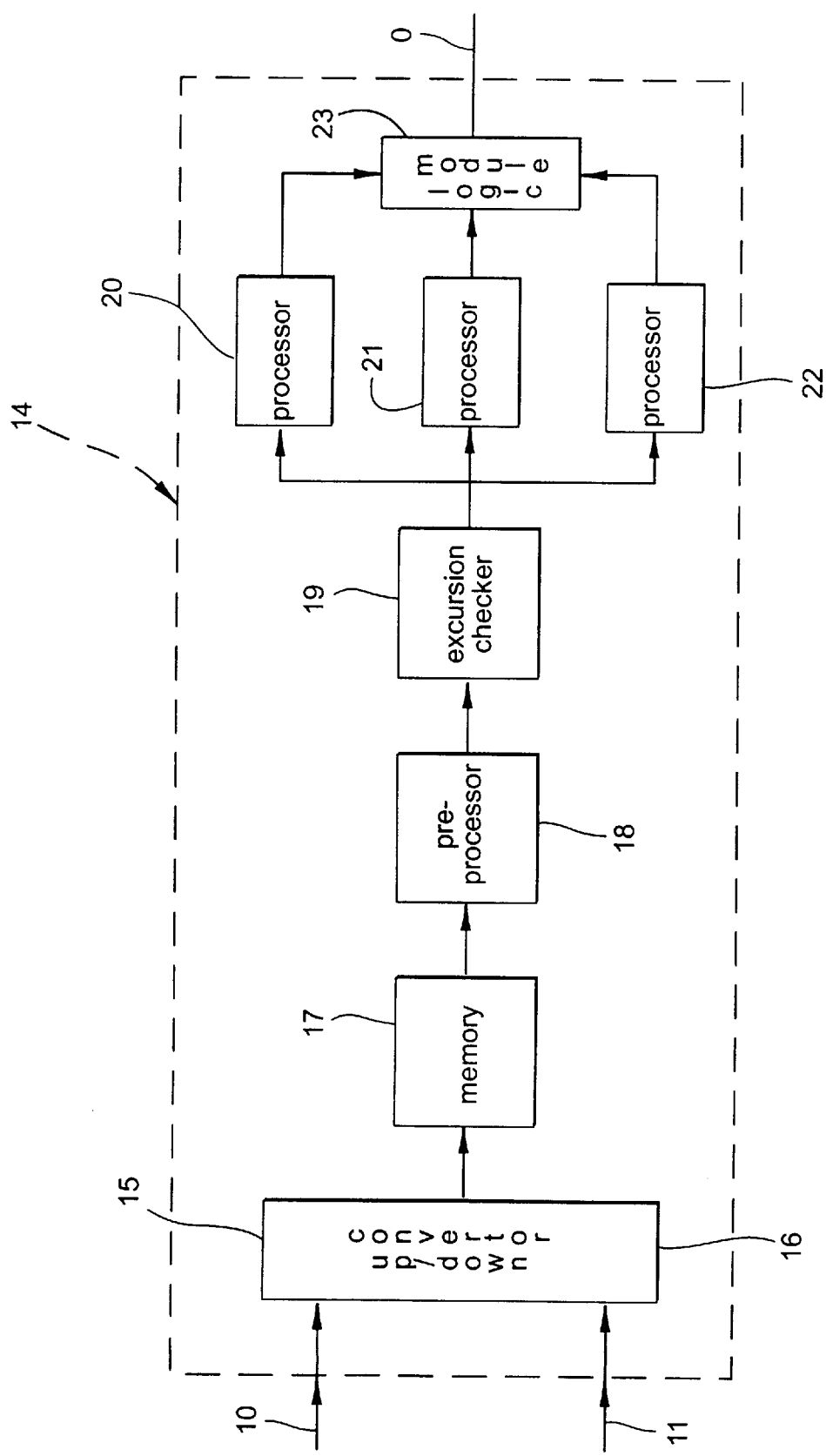
FIG. 5 is a detailed block diagram of the processing unit shown in FIG. 2, illustrating how some of the signals represented in FIGS. 3 and 4 are processed.

As can more easily be seen in the block diagram in FIG. 5, which is a more detailed block diagram of processing unit 14, the two signals on lines 10 and 11 are sent to the input of an up/down counter 15 in such a way that, for example, each signal pulse V10 causes the value of the counter to increase by one unit, while each pulse from signal V11 causes it to decrease by one unit. The counter is zeroed in relation to the stimulus (measured on input 16, derived for example from block 5) and the count is subsequently enabled to start a certain time after the stimulus which the system requires to follow and reach the initial value of the stimulus post-potential. For example, this value may be selected to be around 10 milliseconds.

The values progressively adopted by the counter during a useful window of approximately 50 to 60 milliseconds are periodically read (e.g., every 4 milliseconds) and accumulated in memory 17. Advantageously, memory 17, which usually has a capacity such as to permit the storage of at least 16 to 20 of the values considered in memory may in fact be included in the stimulator device.

In an alternative implementation the signals present on lines 10 and 11 can be sent respectively to the up-count and down-count enable inputs of an up/down counter, in which the clock input is supplied with a periodical signal at a fixed frequency. It is obvious that in this case the progress of the count will also be proportional to the derivative of the input signal with respect to time.

The values taken from memory 17 are then subjected to a pre-processing operation performed in a block 18 generally comprising mild digital filtering designed to reduce the spectral content at higher frequencies (e.g., above 70 Hz). The succession of values in question is then differentiated and again mildly filtered. Finally the values so obtained are translated in such a way that the last of them is always zero. In other words, the value for the last sample is subtracted from each. Those who are skilled in the art will moreover appreciate that the aforesaid pre-processing operation can be performed upstream of memory 17 instead of downstream of it, and therefore before the values are loaded into the memory itself.

To arrive at the final result (generation of output signal O identifying the fact that stimulation has achieved the desired capture effect) a number of logical criteria are applied to the sequence of values obtained from pre-processing. In general it is maintained that the stimulus has been effective as soon as a criterion yields an affirmative result. If a criterion yields a negative result, it then goes on to the next criterion. If all the criteria applied yield a negative result, it is taken that the stimulus has not been effective as a result of failing to satisfy the criteria (default).

Preferably, before the above criteria are applied to the sequence of values which have to be processed another checking action is applied (in block 19) to establish whether the sequence of values in question has an excursion (understood as the difference between the maximum and the minimum value) less than a predetermined limit. In this case it is taken that there has been no capture because a signal is lacking.

Where the above-mentioned sequence of values shows an excursion greater than the threshold value identified by the signal absence threshold, the values in question are subjected to the logical criteria shown diagrammatically in FIG. 5 in the form of three blocks 20, 21 and 22 designed to flow into logic module 23 which carries out a possible combination of these criteria on the basis of means which are better described below.

Those skilled in the art will moreover appreciate that all the operations illustrated by the functional blocks indicated by references 15 to 23 in the diagram in FIG. 5 may in fact be performed within the scope of a single processor (such as e.g., a microprocessor) programmed in accordance with criteria known to those skilled in the art once the envisaged processing objectives are known.

The first criterion represented by block 20 consists of summing all the negative values which are greater in absolute value than an appropriate threshold. If this value exceeds a predetermined limit, the stimulus is declared to be effective through a criterion which can be defined as the negative difference integral.

The criterion illustrated by block 21 consists of checking whether the maximum value (in modulus and sign) adopted by the samples is greater than the first value increased by a suitable quantity. In this case it declares that the stimulus is effective on the basis of increasing difference criterion.

The third criterion, represented by block 22, is more complex. This consists of reducing the series of samples to a series of segments of straight line which provide a better representation on the basis of a specific method of approximation (e.g., a simplified best fit method on four segments in the proposed example implementation). From the segments representing the approximation the angular coefficients are then taken and these are compared with four pairs of limiting values calculated in accordance with a predetermined algorithm (which itself does not have any effect on the features of the invention). If at least one of the angular coefficients is not included between the corresponding pair of limiting values it is deduced that the stimulus has been effective on the basis of a best fit segmented analysis criterion.

It should be appreciated that an equivalent procedure consists of standardizing the values of the four angular coefficients with respect to one of them, for example the first, and then applying comparison with the pairs of thresholds (after these also have been normalized) to the remaining three values. The criterion in question is only applied if the sequence of values which have to be processed has an excursion (understood as the difference between the maximum value and the minimum value) which is greater than a predetermined limit. Otherwise the outcome from the two preceding criteria applies.

The combination of criteria represented by blocks 20, 21 and 22 (it will also be remembered that, preferably, the stimulus is considered to be effective as soon as a criterion yields an affirmative result, going on to the next criterion if a criterion yields a negative result) is carried out by the block indicated by 23, which in fact generates the output signal O with different logic values (e.g., "1" or "0", respectively) depending upon whether the stimulus can be regarded as being effective or not.

To sum up, the solution according to the invention has many advantages. Firstly, it can be used to detect the possible existence of an evoked response superimposed on the stimulation artifact without using analog or digital techniques to attenuate or eliminate the post-stimulation polarization artifact. Also it does not require the use of special electrodes to perform the operation, neither bipolar electrodes nor electrodes having low polarization characteristics. Also it does not require long recovery times after the stimulus but can be made operational within a few milliseconds of the stimulus itself. Furthermore it does not make assumptions which are not broadly applicable with regard to the shape of the analyzed wave and therefore knowledge of reference samples for the signal is not required. The solution according to the invention therefore makes it possible to process the signal independently of any stimulus, making it possible to detect capture stimulus by stimulus even when there are changes in the characteristics of each stimulus with respect to the previous one. Furthermore this does not require the emission of close pairs of stimuli to perform the operation and also makes it possible to decide on the effectiveness of each stimulus within a predetermined time with the possibility of immediately engaging in any corrective action (e.g., the emission of a back-up stimulus). The analysis algorithm is independent of the precise profile of the evoked response and is therefore potentially effective in a wide spectrum of cases. Through detecting the evoked response the system makes it possible to achieve an increase in the useful life of the stimulator, maintaining the energy of stimulation within minimum values compatible with the requirement for effective stimulation. Furthermore the system makes it possible to follow any changes in the stimulation threshold, due either to post-implant changes or changes of a physiological nature (e.g., daily fluctuations), thus increasing the reliability of stimulation.

What is claimed is:

1. A device for determining the effectiveness of electrical stimulation of heart muscle from a signal comprising a post-potential component having, in the event of effective stimulation, a superimposed evoked response component, the device comprising:

a differential stage with a first input for application of the signal and a second input for application of a feedback signal, the differential stage generating a corresponding output signal whose level is determined by the levels of the signals present at the first and said second inputs; and a comparator stage including a feedback unit configured to act on the second input in a follower relationship to the signal present at the first input avoiding saturation of the differential stage;

the feedback unit being configured to generate at least one compensating signal indicative of the variation of the signal present at the first input over time, the at least one compensating signal being indicative of the presence of the evoked response.

2. The device according to claim 1, wherein the comparator stage comprises at least two threshold levels which when reached by the output signal from the differential stage are indicative of possible saturation of the differential stage relative to its linear functioning dynamics.

3. The device according to claim 2, wherein the comparator stage comprises at least one further threshold defining a field of values for the output signal from the differential stage in which the feedback unit is substantially inactive.

4. The device according to claim 1, wherein the feedback unit is configured to generate first and second compensation signals which are indicative, respectively, of the divergence between the output signal from the differential stage in a first and a second direction, respectively, with respect to a selected reference level.

5. The device according to claim 4, wherein the feedback unit is configured to apply a signal obtained from the sum of the first and the second compensation signals to the second input of the differential stage.

6. The device according to claim 5, wherein the sum is obtained with different signs for the first and said second compensation signals, respectively.

7. The device according to claim 1, wherein the feedback unit comprises an integrator stage configured to generate a signal applied to the second input by integration.

8. The device according to claim 1, wherein the at least one compensating signal is a pulsed signal in which the frequency of the pulses is indicative of the difference between the output signal from the differential stage and a selected reference level.

9. The device according to claim 1, wherein the comparator stage is configured to generate first and second compensation signals of the pulsed type, in which the pulse frequency is indicative of the derivative of the signal present at the first input with respect to time, the first and second compensation signals being generated alternately between them according to the sign of the derivative.

10. The device according to claim 9, further comprising a counter and wherein the first and second compensation signals are input respectively as increasing and decreasing signals to the counter, the progression of the count in the counter over a selected period of time comprising a sequence of count signal values indicative of the effectiveness of the stimulation pulse.

11. The device according to claim 10, wherein the counter is configured so as to be zeroed corresponding to the action of electrically stimulating the heart muscle.

12. The device according to claim 11, wherein the counter is enabled after a predetermined time interval following stimulation of the heart muscle.

13. The device according to claim 10, wherein the counter is configured to be enabled for the purposes of performing the corresponding count during a time window of a size determined from the stimulating effect.

14. The device according to claim 13, wherein the time window has a duration ranging from 50 to 60 milliseconds.

15. The device according to claim 10, further comprising a processing logic module which is capable of applying to the count signal values from the counter during the selected period of time at least one criteria for identifying the effectiveness of stimulation selected from the group of:

1) whether the sum of all the negative values which are greater in absolute value than a selected threshold value exceeds a predetermined limit, 2) whether the maximum value of the count signal values, in modulus and sign, is greater than the first value of the count signal values incremented by a specified amount, and 3) whether reduction of the sequence of the count signal values by interpolation into a series of segments of a straight line identified by their corresponding angular coefficients, with subsequent comparison of the angular coefficients with corresponding pairs of selected limit values results in at least one of the angular coefficients exceeding the corresponding pair of limit values.

16. The device according to claim 15, wherein the processing logic module is configured to generate an output signal indicative of effective stimulation when an affirmative result is obtained from one of the criteria.

17. The device according to claim 16, wherein the processing logic module is configured to apply the criteria in sequence, passing on to the next criterion if a negative result is obtained from one of the criteria.

18. The device according to claim 15, wherein the processing logic module is configured to generate an output signal indicative of ineffective stimulation when all three of the criteria yield a negative outcome.

19. The device according to claim 14, further comprising means for detecting excursion of the count signal values during the selective period of time between a selected maximum and a selected minimum value and for declaring that the stimulating action is ineffective if the detected excursion is less than a predetermined limit.

20. The device according to claim 15, wherein the processing logic module is configured to detect a difference between a maximum value and a minimum value of the sequence of count signal values subjected to the third criterion and to apply the third criterion only if the difference between the maximum value and the minimum value is greater than a predetermined limit.

21. The device according to claim 20, wherein the processing logic module is configured to avoid application of the third criterion when the difference between the maximum value and the minimum value is less than the predetermined limit.

22. The device according to claim 15, further comprising at least one processing logic module selected from:

a filtering module to reduce the spectral content of the signal transferred to the logic module at higher frequencies, a module to differentiate the sequence of values subjected to the filtering, and a module to translate the values obtained from this differentiation in such a way that the last of them is always zero.

* * * * *